Figure 3:
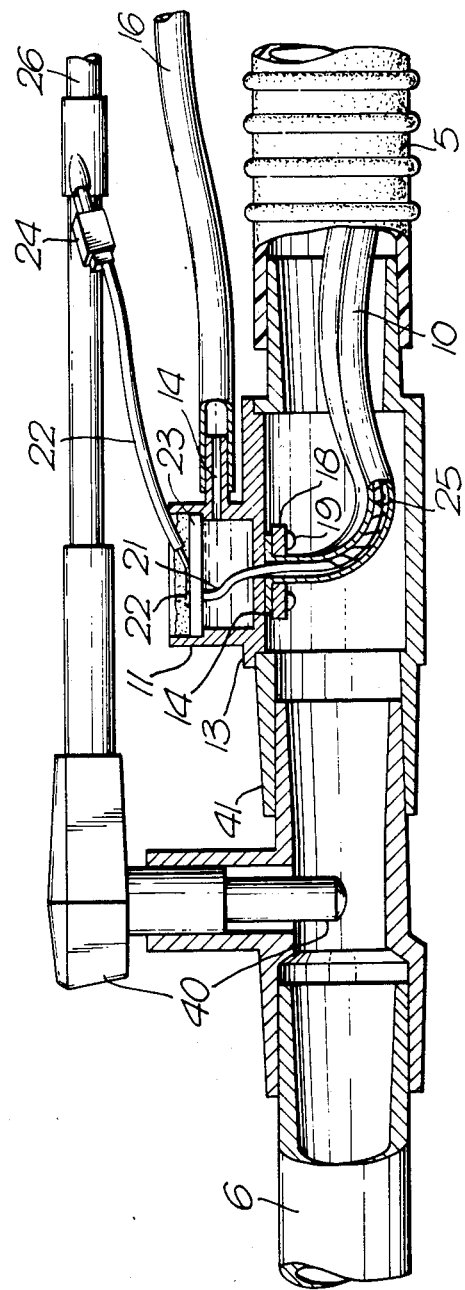

United States Patent [19]

Elsworth et al.

[11] Patent Number: 4,708,831

[45] Date of Patent: Nov. 24, 1987

[54] METHODS OF AND/OR APPARATUS FOR HUMIDIFYING GASES

[75] Inventors: Adrian J. Elsworth; Michael G. Daniell; Paul Zwaan; David P. M. Stewart, all of Auckland, New Zealand

[73] Assignee: Fisher & Paykel Limited, Auckland, New Zealand

[21] Appl. No.: 865,884

[22] Filed: May 21, 1986

[30] Foreign Application Priority Data

May 22, 1985 [NZ] New Zealand .................... 212163
Dec. 23, 1985 [NZ] New Zealand .................... 214694
Feb. 12, 1986 [NZ] New Zealand .................... 215123

[51] Int. Cl.$^4$ ........................................... A61M 16/16
[52] U.S. Cl. .................... 261/130; 261/142; 261/104; 261/DIG. 65; 128/203.27; 128/203.17; 128/204.13; 604/253; 219/497
[58] Field of Search ............... 261/130, 131, 142, 104, 261/DIG. 65; 128/203.27, 203.17, 203.14, 204.13; 604/253; 219/497

[56] References Cited

U.S. PATENT DOCUMENTS

| | | |
|---|---|---|
| 3,102,537 | 9/1963 | Bartlett . |
| 3,616,796 | 11/1971 | Jackson ........................ 128/203.27 |
| 3,789,190 | 1/1974 | Orosy et al. .................... 219/497 |
| 3,871,373 | 3/1975 | Jackson . |
| 3,881,482 | 5/1975 | Lindholm . |
| 3,920,009 | 11/1975 | Olsen . |
| 3,990,441 | 11/1976 | Hoyt et al. .................... 128/203.27 |
| 4,038,980 | 8/1977 | Fodor ........................... 128/203.27 |
| 4,038,982 | 8/1977 | Burke et al. .................... 604/253 |
| 4,090,513 | 5/1978 | Togawa . |
| 4,137,940 | 2/1979 | Faisandier .................... 604/253 |
| 4,367,734 | 1/1983 | Benthin . |
| 4,381,267 | 4/1983 | Jackson . |
| 4,430,994 | 2/1984 | Clawson et al. . |
| 4,461,735 | 7/1984 | Wirt . |
| 4,477,395 | 10/1984 | Albarda .......................... 128/203.14 |
| 4,564,748 | 1/1986 | Gupton .......................... 128/203.17 |
| 4,621,632 | 11/1986 | Bartels et al. .................. 128/203.17 |

FOREIGN PATENT DOCUMENTS 2221156 11/1974 France ........................... 128/203.27

Primary Examiner—Tim Miles
Attorney, Agent, or Firm—Heslin & Rothenberg

[57] ABSTRACT

A humidifier has a supply of water suspended on a pole above a patient which supplies water through a removable drop counter of magnetically actuated ball valve to a microporous tube mounted in but mechanically separated from a ventilating line between a ventilator and the patient. The water is heated in the microporous tube to create a vapor pressure sufficient to cause water vapor but substantially no liquid water to pass through the tube into the ventilating line. Electrically energized controls are provided to obviate maloperation and to maintain safe operating conditions including maintaining safe temperature conditions, and prevention of excess water entering the ventilation line by counting the drops of water passing through the bold valve, and closing the ball valve if the count rate is outside desired count rates and power or the monitoring equipment fails.

22 Claims, 8 Drawing Figures

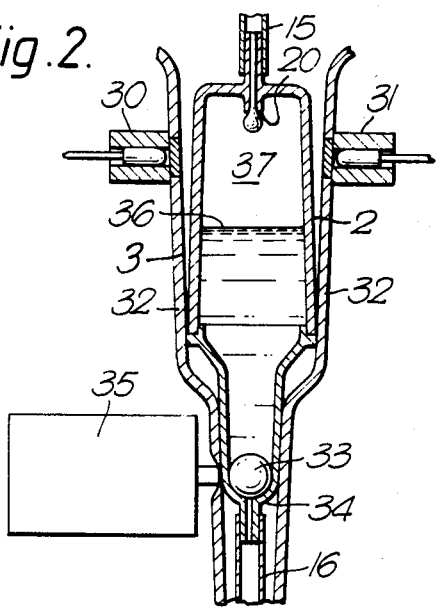
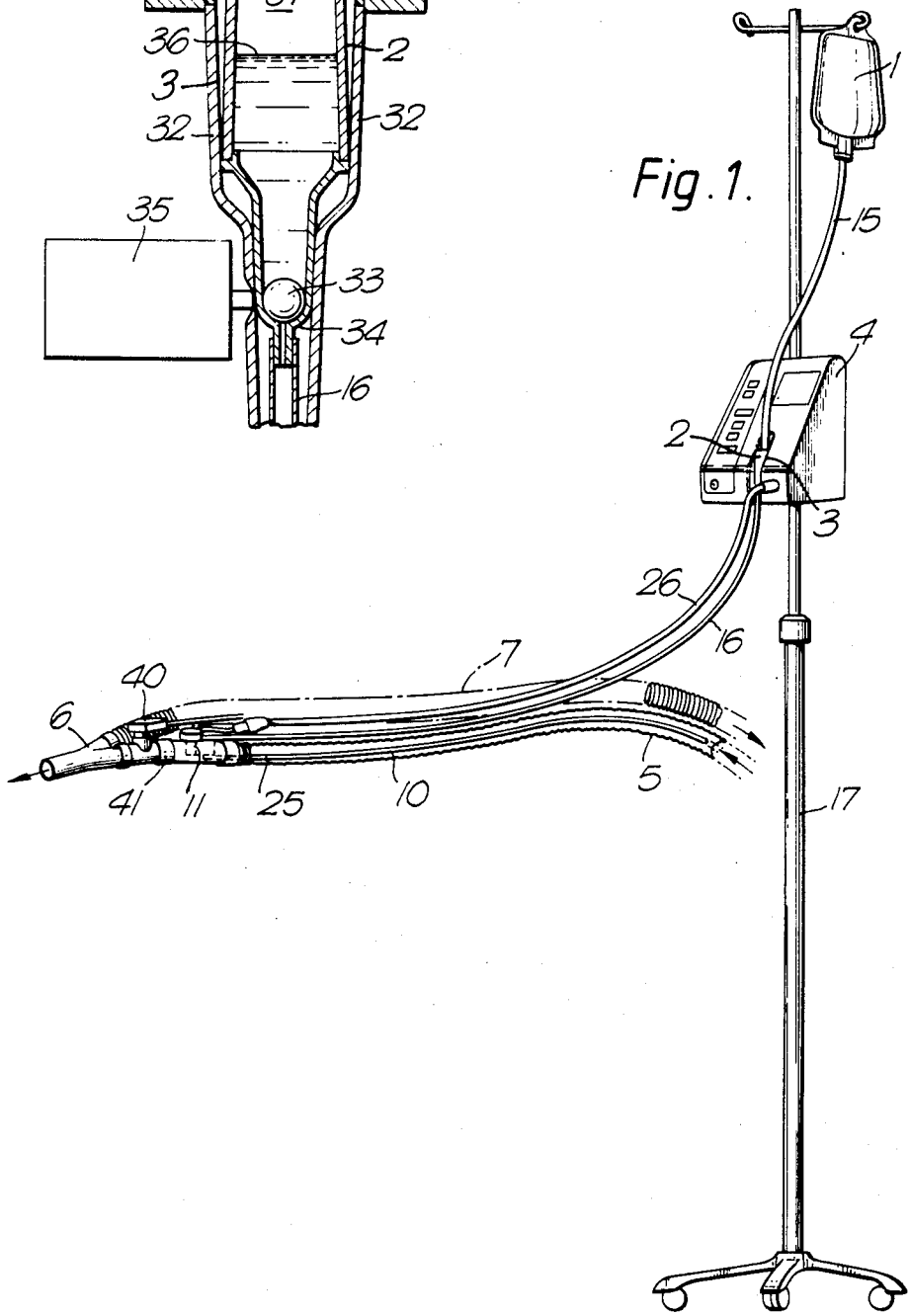

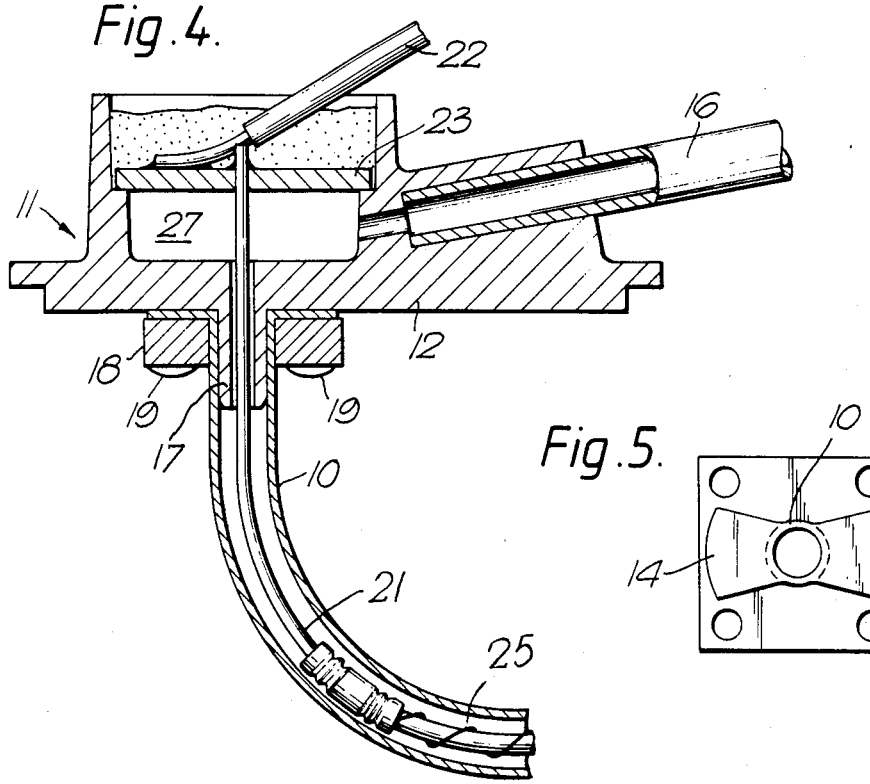
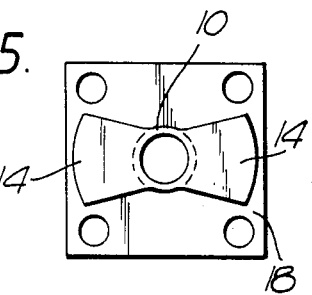
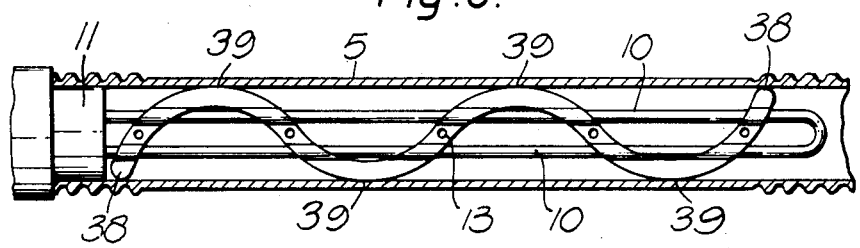
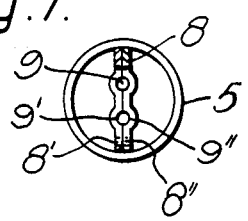

METHODS OF AND/OR APPARATUS FOR HUMIDIFYING GASES

This invention relates to methods of and/or apparatus for humidifying gases and has been devised particularly though not solely for use in providing humidified gases to a patient in a hospital in need of such humidified gases.

It is an object of the present invention to provide methods of and/or apparatus for humidifying gases which will at least provide the public with a useful choice.

Accordingly in one aspect the invention consists in a method of humidifying gases; said method comprising the steps of supplying water into a first passageway by passing the water from a source of substantially constant positive pressure to said first passageway, heating said water, passing gases through a second passageway, causing water vapour but substantially no liquid water to pass through a microporous wall common to both said passageways, said microporous wall being permeable to water vapour but substantially impermeable to liquid water, the water vapour passing through said microporous wall to be entrained in the passing gases to humidify said gases for transmission to a point of use, monitoring the temperature of the humidified gases, causing changes in temperature of the humidified gases to cause changes in the supply of heat to said water to maintain the temperature of humidified gases within a desired range of temperatures, monitoring the rate of flow of water of said first passageway, comparing the monitored rate of flow of water in said first passageway with a desired rate of flow of water therein, and causing a cessation of flow of water in said first passageway and heat to said water on the monitored rate of flow of water and the desired humidified gases temperature and the power delivered varying more than a desired amount from said desired rate of flow, desired temperature, and delivered power.

In a further aspect the invention consists in apparatus for humidifying gases; said apparatus comprising a first passageway, water supply means for supplying water to said first passageway, a second passageway through which gases are supplied to a microporous wall common to both said first passage and said second passage at a point of use, said microporous wall being permeable to water vapour but substantially impermeable to liquid water, means to supply heat to said water to generate a vapour pressure within said first passageway sufficient to cause passage of water vapour but not liquid water through said microporous wall, a control unit including temperature monitoring means to monitor the temperature of said gases close to said point of use, water flow monitoring means to monitor the rate of the flow of water to said first passageway, means to compare the monitored rate of flow thereof with a desired rate of flow, and means to cause cessation of flow of water and of heat to said water on the monitored rate of flow of said water or the desired temperature of said gases varying by more than a desired amount, the construction and arrangement being such that on gases being passed through said second passageway tube over the surface of said microporous wall, water vapour but substantially no liquid water passes through the walls of said first passageway to be entrained in said gases passing through said second passageway and over said microporous wall.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

Figure 8:
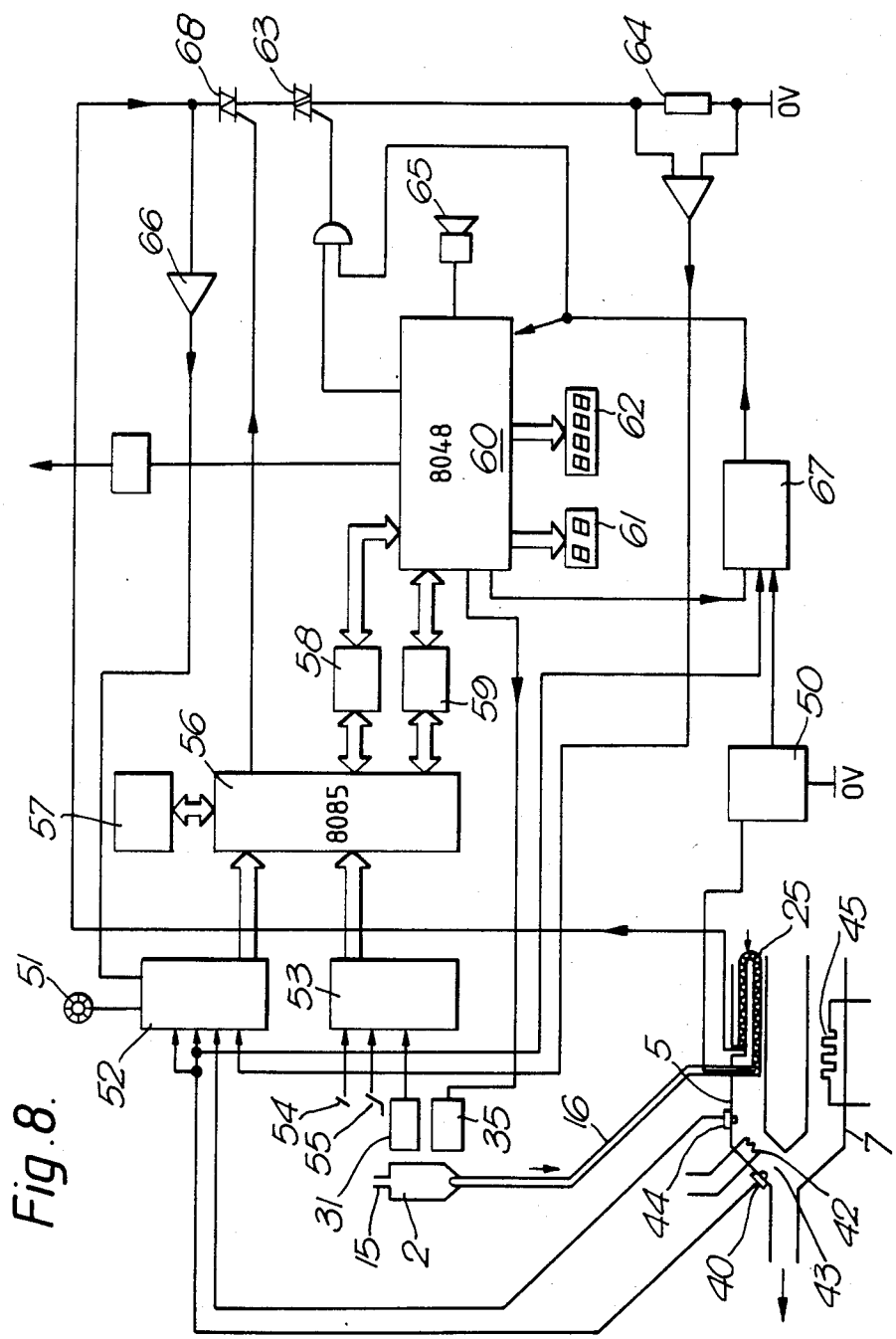

One preferred form of the invention will now be described with reference to the accompanying drawing in which, FIG. 1 is a diagrammatic view of apparatus according to the invention, FIG. 2 is an enlarged diagram of a valve constructed according to part of the invention, FIG. 3 is an enlarged view of part of FIG. 1, FIG. 4 is a further enlargement of a termination arrangement, FIG. 5 is a view of part of FIG. 4, FIG. 6 is a diagrammatic cross section of an inspiratory line with a microporous tube supported therein by a separating means, FIG. 7 is a cross section of the construction of FIG. 6, and, FIG. 8 is a diagram of apparatus used in the invention including a block diagram of electronic circuitry used in the invention.

Referring to the drawings, particularly FIGS. 1 and 2, and according to the invention, humidifying apparatus is provided as follows: a water supply bag 1 provides water to a drip chamber 2 removably mounted in a shaped slot 3 of a casing 4 containing a control unit which will be described in detail later. An inspiratory line 5 leads from a breathing machine e.g. a ventilator (not shown) of orthodox construction and use and gases pass through the inspiratory line 5 from the ventilator to a Y junction 6 which in turn is connected to a mask or other device which enables the gases to be supplied to a patient. An expiratory line 7 is connected to the Y junction 6 and passes expired gases to an exhalation valve (not shown). Lines 5 and 7 are preferably flexible corrugated, tubes or the like made of a suitable synthetic resin material e.g. polyethylene.

A humidifying element is provided comprising a microporous tube 10 having the property of being permeable to water vapour but substantially impermeable to liquid water for example made of expanded PTFE (poly tetra fluoro ethylene) and the tubing is preferably flexible, inert and hydrophobic. Such a tubing is manufactured under the trade mark GORE-TEX and is available from W. L. Gore & Associates Inc. Newark, Del, U.S.A. in various diameters from 1 mm to 12 mm inside diameter. Microporous structures of such tubing are available having 2.0 micro meters to 3.5 micro meters passageways therethrough. The tube 10 is looped and the free ends are mounted in a termination block 11. Tube 10 is positioned in line 5 and is supplied with a supply of water from the bag 1 through tube 15, drip chamber 2 and tube 16, and provides a common wall between water in the tube 10 and gases in the inspiratory line or tube 5. The tube 10 is mounted within the line 5. The inspiratory line or tube 5 may for example be of any useful diameter and length for example 20 millimeters inside diameter and about 600 millimeters in length. The tube 10 may be arranged in a single length or may be arranged as a helix or bunched as desired to give the desired vapour transmission rate. Preferably however the tube 10 is looped as more clearly shown in FIGS. 3 and 6. The water supply bag 1 is a flexible bag suspended at a convenient level e.g. on a mobile pole 17 to give a desired static head.

In FIG. 2, tube 15 leads to an orifice 20 in the drip chamber 2 and the orifice 20 is dimensioned to supply drops of water falling through air space 37 in the chamber 2.

The drip chamber 2 is shown in more detail in FIG. 2.

Water passes from orifice 20 as a series of drops and each drop falling through air space 37 gives a signal through interruption of an infra red beam from an infra red transmitter 30 to an infra red receiver 31 which is referred to as drop detector 31. The housing walls 32 of the slot 3 are tapered so that the drip chamber 2 and associated tubes 15 and 16 may be readily placed in position and removed without interference with other parts of the control unit in casing 4. This is of considerable advantage since it enables "throw away" or separately sterilizable "plumbing" assemblies to be used, leading to good hygiene.

Mounted within the tube 10 is a looped heating element 25, FIG. 3, with the two free ends of the loop each crimped to an interconnecting wire 21 which in turn is connected by soldering to a printed wiring board 23 and in turn to one of a pair of leads 22 and via a connector 24 and cable 26 to the control unit in casing 4.

A suitably resistive heating element wire is used, and to reduce risks of overheating, the heating element is preferably a low melting point material. Changes in resistance due to temperature changes of the heating wire are used to give an approximate measurement of the wire and water temperature. The heater wire preferably has a readily measurable temperature coefficient of resistivity. Wattage input for the heating element 25 can be quite high, suitable operating parameters being for example 2 4 V, 125 W.

The melting point of the element wire is preferably less than the melting point of the material of tube 10. Where the material of tube 10 is of GORE-TEX which has a melting point of about 350° C., a suitable material for the element wire 25 is a tin-silver alloy having a melting point of about 230° C.

The heating element wire 25 is preferably "cold ended," e.g. by crimping, welding or brazing the element wire 25 to the low resistance e.g. copper wires 21 to enable the ends of wire 25 to run cooler than the main run of wire 25 and reduce the risk of overheating the ends. The terminal block 11 and details thereof are shown in more detail in FIGS. 3 to 5. As illustrated in FIG. 4, for example, terminal block 11 comprises a body 12 having an inner chamber 27 therein and a nipple member 17 projecting therefrom which defines a flow communication passage into chamber 27. The ends of tube 10 are positioned concentrically over a nipple member 17 as illustrated in FIGS. 4 and 5. The ends of the tube 10 are preferably split and the two or more resulting strips 14 turned outwardly normal to the longitudinal axes of the tube and a thick flange member 18 clamped in place concentrically over tube 10 and nipple 17 by rivet means 19 in flange member 18. Flange member 18 retains strips 14 between body 12 and flange 18 and also retains tube 10 on nipple 17 by rivets 19 into the block 11 to connect tube 16 with preferably both ends of the tube 10, there being an opening from a chamber 27 to the passageway of tube 10.

To maintain separation between the line 5 and the line 10 separating means are provided as illustrated in FIGS. 6 and 7. The separating means preferably comprise a longitudinal sinuous member 8 made for example of a suitable synthetic resin material e.g. a polypropylene homopolymer and, as may be seen from FIG. 7, the sinuous member 8 is made of two strip sections 8' and 8" each section being provided with semi-circular grooves 9' and 9", respectively to provide, when assembled as shown in FIG. 7, a circular aperture 9. The apertures 9 are arranged on the sinusoidal line of member 8 so that they are in longitudinal alignment and tube 10 is inserted or positioned in apertures 9 and is thereby supported at frequent intervals with the upper and lower arms of the tube 10 being maintained in spaced relationship from each other and from the wall of line 5 as may be seen from FIG. 6. The sinusoidal member 8 is arranged to have joining means preferably in one member, such as studs 13 at intervals in one member 8' or 8" and holes in the other member 8' or 8" respectively, the studs 13 fitting tightly in the holes to enable the two members 8' and 8" to be clipped together with the microporous tube 10 in the defined apertures 9 therebetween. In this way, sinusoidal bends 39 of the member 8 are fitted against the line 5 and since ends 38 are also so fitting, the tube 10 will be supported separated from the line 5.

In use hot water is supplied to the tube 10 at for example 80° C. It is of course undesirable that a tube containing water at this temperature should have direct contact with the line 5 which may be resting on the bare chest or other part of the patient's body. Accordingly this form of the present invention obviates or minimises a risk of the high temperature part of tube 10 being in a position to transmit heat by direct contact between the tube 10 and line 5 and then to a patient's body. Additionally at least in the preferred form there is a considerable improvement in heat transfer performance over an unsupported microporous tube.

Referring again to FIG. 2, the drip chamber 2 contains a water exit valve comprising a ferro magnetic (e.g. steel) ball valve member 33 which rests in and covers a funnel-like water exit ball valve seat 34. Ball valve member 33 is displaced sideways relative to the flow of water through seat 34 by applying current to an electromagnet 35 disposed within the casing 4 to permit flow of water from the drip chamber 2 to the tube 16. Since the flow rate is low, only a small displacement is necessary as between open and closed positions of the ball 33. The ball is held in the closed position by gravity and the static pressure of the water.

The pool of water in the drip chamber 2 is maintained at a suitable level 36 so that the drops fall through an air space 37 from the orifice 20 to the level 36. This level is substantially maintained automatically once set because an increase in height of level 36 increases the air pressure in air space 37 and reduces the hydrostatic force which causes the formation of drops.

As illustrated in FIGS. 1 and 3, air temperature sensing element 40 e.g. one or more preferably two thermistors is or are removably positioned in the inspiratory line 5 downstream of the heater 25. The actual position depends on the amount of cooling of the gases desired. To obtain adequate humidification of the gases it may be desirable to heat the gases to a higher temperature than that desired, and to allow cooling to 100% RH. The heated water in tube 10 heats the gases in tube 5 and the heating to a higher temperature results in the gases attaining a higher than desirable temperature—say 38° C. The gases are then cooled by passing through a cooling tube 41 positioned between the tube 5 and the sensing element 40 in the Y junction 6. The length of the tube 41 gives some control over humidity.

Alternatively or in addition an auxiliary heater 42 FIG. 8, is positioned in or adjacent the inspiratory section 43 of the Y junction 6, and, to assist in controlling the heat and humidity an auxiliary air temperature sensing element 44 is provided between the heater 25 and the auxiliary heater 42.

Also a heating element 45 may be positioned in the expiratory line 7 to prevent condensation and/or to condition expired gases for further treatment in the ventilator and return to the patient if desired.

Referring now to the schematic diagram of FIG. 8, an electrical transformer is provided in power supply system 50. Preferably changes in resistance of the heater element 25 due to temperature changes of that element are used to provide electrical signals which activate control of power supply 50 to supply appropriate power to the heating element 25. These signals and signals from the air temperature sensing devices 40 and if provided 44 are supplied to an analogue to digital converter which is preferably a multiplexed arrangement, and a set temperature control 51 also supplies signals to the analogue to digital converter 52. Signals from drop detector 31 are supplied to a binary input interface 53, and manually operated "mute" and "function" switches 54 and 55 are also provided to this interface. The convertor 52 and the interface 53 feed an 8085 microprocessor 56 with which is associated a memory 57. The 8085 microprocessor 56 and a further 8048 microcontroller 60 are interconnected through a mutual surveillance connection 58 and data interface 59. The interconnection 58 enables the 8048 microcontroller 60 to check on proper performance of the 8085 microprocessor 56 and to enable the microprocessor to check on the operation of the microcontroller 60. The micro controller 60 supplies a water useage display 61 and an air temperature display 62. The noted transformer in power supply 50 supplies the heater 25 through a main heater Triac 68, and a backup Triac 63. The current sensor 64, an alarm 65, a voltage sensor 66 and other electronic backup equipment provided in the form of an analogue backup 67 are interconnected with the remaining apparatus. The current sensor 64 and the voltage sensor 66 enable the resistives of the heater element 25 to be calculated to give an indication of the temperatures of that element. The analog to digital converter 52 acts with the analogue back up 67 maintaining a check on the voltage output of the power supply 50.

The operation of the apparatus is as follows.

An operator brings the support pole 17 carrying the control unit in its casing 4 to a patient. The operator then sets up the "plumbing" comprising the water bag 1 which may be a normal intravenous supply water bag, the tube 15, the drip chamber 2, the tube 16 and interconnect this equipment with the inspiratory line 5 connected to the Y piece 6 which in turn is connected to a mask or other device for administering gases to a patient. Because the temperature sensing device (thermistor) 40 is removable and the leads 22 connect to leads 26 through the plug and socket 24 ready interchange of the tubes 5 and 10 is possible. It is to be noted that the "plumbing" may be provided as a new sterilized piece of equipment for each patient and this provides considerable advantages in getting the equipment quickly into use.

With power off in the control unit, the operator then causes water to flow into the drip chamber 2. Since the magnetic ball valve member 33 rests on its seat 34, the valve is closed and the water level in chamber 37 builds up by drip flow until air pressure in chamber 37 inhibits further drop formation. The operator then turns on power supply to the control unit and as a result the magnetic ball valve is opened and water flows into the tube 10 and is heated therein to a desired temperature. By virtue of the nature of the wall of the tube 10 permitting water vapour but substantially no liquid water to pass, water vapour passes into gases flowing over the outer surface of the tube 10 i.e. within the inspiratory line 5. The static water pressure gives a water pressure sufficient to cause flow of water to the tube 10 and prevents back flow of water vapour up tube 16. The demand for water depends on the passage of water vapour but substantially no liquid water through the microporous wall of the tube 10, and passage of water vapour depends on the difference between water vapour pressure in tube 10 and water vapour pressure in tube 5. The water vapour pressure in the inner tube 10 is controlled by the temperature sensor 40. Thus the temperature of the gases delivered to the patient is sensed by thermistor 40, and controlled amounts of heat are supplied by the heating element to the water in tube 10 under control of the microprocessor 56 in response to signals from the thermistors 40. Signals are passed from the temperature sensors 40 (and 44 if provided), and the change in resistance of the heater element 25. The drop detector 31 signals together with the convertor signals are fed to the 8085 microprocessor 56 and in turn signals are supplied to the microcontroller 60 which controls the amount of heat supplied to the heating element 25. Counts are indicated at 61 as to the number of drops per minute and the air temperature display 62 receives signals from the 8048 micro controller and in the event of maloperation the alarm 65 is operated. In addition the valve solenoid 35 is energized to keep the ball member 33 off its seat 34 to permit water to pass to the tube 10. In the event of maloperation of the water delivery rate this solenoid 35 is deenergised causing closing of the valve. Thus there is a major safety advantage in that it is not possible for water to pass through the apparatus unless electrical power is switched on to the magnet 35 in particular and to the control unit in general so that it is not possible for water to flow through the apparatus without the control unit being in operation.

The outline of the software programme provided to achieve the above and to provide safe operation and protection against maloperation is as follows.

A. BACKUP/OUTPUT MICRO-PROCESSOR (60)

This processor has three primary functions:
(a) To act as a safety backup. The two processors in the system each have independent airway temperature sensors, and each processor is able to turn off the heater independent of the other. The backup processor detects temperature anomalies in conjunction with the analogue backup circuit.
(b) It processes some of the system outputs.
(c) Each processor in the system checks that the other is operating correctly via the watchdog interface (58).

SOFTWARE OVERVIEW FOR BACKUP MICRO PROCESSOR

Self test
Initialise

Start 8085
Start watchdog timeout

MAIN LOOP

Do forever
  update serial communications output
  update alarm state, dependent on analogue fault input and logical processor flag
  operate solenoid
  operate spare outputs as instructed by control processor
  operate fault simulator
  if backup or co-processor fault, go to a safe condition
**Other tasks are actioned on an interrupt basis.

EVERY AC ZERO CROSSING

Start AC peak timer. AC peaks are communicated to the control processor (56) to enable it to take voltage and current readings from the heater.
Receive data from logical processor
Reset watchdog timer

TIMER INTERRUPT

Update alarm outputs
Generate a pulse indicating AC peak if it is a peak interrupt
Check logical control processor (56) is running, and has not been recently restarted
If logical processor is not running:
  make all outputs safe
  attempt to restart it three times
  alarm if it does not restart
If logical processor requires frequent restarts:
  make all outputs safe
  alarm

B. LOGICAL/CONTROL PROCESSOR (56)

This processor primary task is the control and performance algorithms. It analyses all system inputs and controls the outputs.

SOFTWARE OVERVIEW FOR CONTROL MICRO PROCESSOR

Initialise
Do forever
  calibrate
  control temperature to set value
  display temperature
  display water consumption
  detect fault conditions
  take action on faults
  detect water
  communicate
  detect function input(s)
  take action on function inputs end do

EXPANSION OF EACH OF ABOVE MODULES

Initialise
  set all outputs to safe condition
  self test ROM, RAM, ports, watchdog
  user visible tests
  check valve operation
  calibrate
  detect function inputs

CALIBRATE

Determine mains frequency
Determine heater wire type
Check reference temperatures

CONTROL TEMPERATURE TO SET VALUE

Read set knob
Read and moving average thermistors
Apply heater wire on/off algorithm
Control expiratory heater
Control auxiliary heater

DISPLAY TEMPERATURE

Display a moving average temperature

DETECT WATER USED

Detect occurrence of drop

DISPLAY WATER CONSUMPTION

Calculate weighted average mls per min.
Display for each drop detected
Flash detect light upon drop detection

DETECT FAULT CONDITIONS

Initialise
Disconnect
High airway temp
Low airway temp
Temp probe failure
Water rate high
Water rate low
Triac not on/off
Fault simulator fail
References out of range
Set temp out of range
Water temp high
Water temp low
Too long to warm up
Power to water ratio
System faults

COMMUNICATE

Transmit over an RS 232 standard interface the following:
  water usage
  temperature
  set temperature
  wire temperature
  average power
  status flag
  alarm/error state

DETECT FUNCTION INPUTS

Mute
Mutes alarm for 60s unless new alarm occurs
Initiates recovery from conditions as described
Provides entry to special functions
Auto return to normal operation if not manually returned It is desirable that gases from the ventilator into tube 5 are at a reasonably low temperature—say 25° C. If the gases are at a higher temperature—even as high as say 37° C. humidification is possible by setting the desired operating temperature of sensor 44 at a higher temperature of say 39° C. so that a water vapour pressure difference across the microporous wall of tube 10 can be obtained by heating the water in tube 10 to an even higher temperature—say 45° C. and then cooling the gases in portion 41. Before the sensors 40 are reached, the gases cool down to patient input temperatures of say 37° C. In the event that there is excess, then the auxiliary heater 42 is brought into action.

It will be apparent that the foregoing construction gives a humidifier which is very simple to construct and to use and which does not require material construction or features to put it into operation. In this respect in particular the ready removability and replacement of the "plumbing" i.e. the water supply elements enables the apparatus to be brought in use very quickly.

Further advantages of the present invention at least in the preferred form over present humidifiers are:

1. Because of a reduction in the volume through which the gases must pass better control is possible.
2. Because of a reduction in the volume through which the gases must pass, the gases supplied by the breathing machine (ventilator) are delivered to the patient with less time lag.
3. Because of a reduction of the volume of water which must be heated and because of the proximity of the heated water to the patient, faster and more accurate temperature control is possible.
4. The control of water flow is substantially automatic even though the patient's demand for water vapour varies.
5. Because of the compactness of that part of the apparatus near the patient the sensor and tube 10 may be positioned proximally rather than distally to the patient's head.
6. Because of the proximity of the humidifying element to the patient, heat and water losses and subsequent condensation in the delivery system is reduced.
7. The water flow control valve assists materially in preventing water from being passed to the humidifying device under fault conditions at least assisting in preventing dangerous maloperation.
8. Movement of the ball in the valve up a slope is advantageous in that it reduces the power necessary to move the ball to and hold it in the open position. The ball does not need to be completely lifted off its seat.
9. The display of water usage allow a measure of humidifying performance to be ascertained by a visual check.

What is claimed is:

1. A method of humidifying gases, said method comprising the steps of supplying water into a first passageway by passing the water from a source of substantially constant positive pressure to said first passageway, heating said water by means of an electrical resistance heater in said water in said first passageway, passing gases through a second passageway, causing water vapour but substantially no liquid water to pass through a microporous wall common to both said passageways, said microporous wall being permeable to water vapour but substantially impermeable to liquid water, the water vapour passing through said microporous wall being entrained in the passing gases to humidify said gases for transmission to a point of use, monitoring the temperature of the humidified gases, causing changes in temperature of the humidified gases to cause changes in the supply of heat to said water to maintain the temperature of humidified gases within a desired range of temperatures, monitoring the rate of flow of water of said first passageway, generating electrical signals representative, respectively, of the following parameters:

1. rate of flow of said water to said first passageway,
2. temperature of humidified gases flowing in said second passageway, and
3. heat input to the water in said first passageway, and causing a cessation of flow of water and heat to said water when at least one of said parameters varies from a desired value by more than a predetermined amount.

2. A method as claimed in claim 1 which includes the steps of: supplying water through a drip chamber to said first passageway, while said first passageway is arranged as an inner tube within said second passageway; and continuously counting water drops passing through an air space in said drip chamber to monitor the rate of flow of water to said first passageway.

3. A method as claimed in claim 1 or claim 2 which includes the step of heating the water in said first passageway by passing an electric current through a resistance wire enclosed in said first passageway, said resistance wire having a lower melting temperature than said first passageway.

4. A method as claimed in claim 2 which includes the steps of: using changes in the resistance of said resistance wire to give a signal indicating changes in temperature of the water being heated; and employing a microprocessor to process said electrical signals, said microprocessor being capable of controlling the supply of said heat to said water.

5. Apparatus for humidifying gases, said apparatus comprising a first passageway, water supply means for supplying water to said first passageway, a second passageway through which gases are supplied to a microporous wall common to both said first passageway and said second passageway at a point of use, said microporous wall being permeable to water vapour but substantially impermeable to liquid water, electrical heater means in said water in said first passageway to supply heat to said water to generate a vapour pressure within said first passageway sufficient to cause passage of water vapour but not liquid water through said microporous wall, a control unit including temperature monitoring means to monitor the temperature of said gases close to said point of use, and as a result thereof to cause variation in electrical power delivered to said heater means, water flow monitoring means to monitor the rate of flow of water to said first passageway, means to compare the monitored rate of flow of water with a desired rate of flow, and electrical circuitry and control means, said electrical circuitry and control means comprising means to generate electrical signals representative, respectively, of the following parameters:

1. rate of flow of water in said first passageway,
2. temperature of gases in said second passageway,
3. electrical power to said heater means, said electrical circuitry and control means being adapted to cause cessation of flow of water and of heat to said water when at least one of said parameters varies from a desired value by more than a predetermined amount, the construction and arrangement being such that on gases being passed through said second passageway tube over the surface of said microporous wall, water vapour but substantially no liquid water passes through the walls of said first passageway to be entrained in said gases passing through said second passageway and over said microporous wall.

6. Apparatus as claimed in claim 5 wherein said first passageway is disposed as an inner tube within said second passageway and automatic water level maintaining drip chamber means is connected in fluid flow relationship to said inner tube to supply water thereto.

7. Apparatus as claimed in claim 6 wherein said inner tube is looped within said second passageway, with two free ends thereof both connected in fluid flow relationship to said drip chamber means.

8. Apparatus as claimed in claim 7 wherein separating means are provided within said second passageway and arranged to support said first passageway in a manner such that a separation distance is maintained between said microporous wall and the wall of said second passageway.

9. Apparatus as claimed in claim 8 wherein said separating means comprise at least one longitudinal sinuous member having supports arranged in two longitudinal lines, said first passageway being arranged on said supports in a manner such that said first passageway is supported with clearance from the walls of said second passageway.

10. Apparatus as claimed in claim 9 wherein two longitudinal sinuous members are provided each having semi-circular grooves and said members having joining means to join one to the other with said semi-circular grooves aligned to provide apertures in which said first passageway is supported.

11. Apparatus as claimed in claim 7 wherein the two ends of the loop are fixed in a termination by at least one end of the loop being split into two or more parts which parts are mechanically clamped to said termination.

12. Apparatus as claimed in claim 11 wherein said first passageway contains an electric heating element and heat control means are provided to control the supply of electricity to said electric heating element in a manner such that the quantity of heat supplied to the water in said first passageway is controlled by said heat control means.

13. Apparatus as claimed in claim 12 wherein said electric heating element is formed of a material which will melt at a temperature lower than the melting temperature of the material of said inner tube.

14. Apparatus as claimed in claim 12 wherein said termination includes terminals for said electric heating element which are adapted to run cooler in use than the main part of the heating element.

15. Apparatus as claimed in claim 12 wherein means to monitor the temperature of the water in said first passageway are provided and comprise means to measure the change in resistance of said heating element in said water in said first passageway.

16. Apparatus as claimed in claim 5 wherein said means to cause cessation of a supply of water comprises: a drip chamber connected between said water supply means and said first passageway, a valve in said drip chamber comprising a conduit connected to said drip chamber and said first passageway through which water from said drip chamber is passed into said first passageway, a valve seat at the end of said conduit, a ball valve member arranged to seat on said valve seat to close the valve under static conditions and prevent water from passing from said drip chamber into said first passageway, said valve member being of a magnetic material, and an electromagnet arranged relative to said ball valve member in a manner such that when electrical power is supplied to said electromagnet said ball valve member is displaced sideways in relation to said valve seat.

17. Apparatus as claimed in claim 16 wherein said valve is disposed in a lower part of said drip chamber so that said ball valve member is submerged in the water in said drip chamber.

18. Apparatus as claimed in claim 16 or claim 17 wherein said water supply means and said drip chamber are removably associated with said control unit of said apparatus to permit ready replacement.

19. Apparatus as claimed in claim 5 wherein said water flow monitoring means comprise means to count the number of drops formed per unit of time and passing through an air space and to generate electrical signals representative of said count for supply to said electrical circuitry and control means.

20. Apparatus as claimed in claim 5 wherein said electrical circuitry and control means includes a microprocessor and a microcontroller and said temperature monitoring means includes two temperature sensing devices, one said temperature sensing device sending signals to said microprocessor and one said temperature sensing device sending signals to said microcontroller, said microprocessor and said microcontroller being electrically interconnected in said circuitry and each being effective on an appropriate signal being received to interrupt the supply of electrical power to said heating element independently of the other of said microprocessor and said microcontroller.

21. Apparatus as claimed in claim 20 wherein said microcontroller and said microprocessor are electrically connected to each other through a surveillance connection so that each checks that the other is operating.

22. Apparatus as claimed in claim 20 or claim 21 wherein said electrical circuitry and control means includes means to detect one or more of: high or low gases temperature, temperature sensing devices failure, high or low water supply rate, power supply failure to said heating means, references or set temperature being out of range, high or low water temperatures, lengthy warm up times, incorrect power to water supply ratio and system faults.

* * * * *